United States Patent [19]

Miller

[11] Patent Number: 4,520,806

[45] Date of Patent: Jun. 4, 1985

[54] SPLINT AND METHOD OF USING SAME

[76] Inventor: Larry Miller, 465 Oliveta Pl., La Canada, Calif. 91011

[21] Appl. No.: 495,630

[22] Filed: May 18, 1983

[51] Int. Cl.³ .............................................. A61F 5/04
[52] U.S. Cl. ................................. 128/87 R; 128/89 R
[58] Field of Search ................... 128/87 R, 89 R, 90, 128/83, 165; 273/189 R, 189 A

[56]  References Cited

U.S. PATENT DOCUMENTS

| | | | |
|---|---|---|---|
| 3,117,786 | 1/1964 | Anderson | 128/89 R |
| 3,850,167 | 11/1974 | Seeley | 128/87 R |
| 3,976,062 | 8/1976 | Cox | 128/89 R |
| 4,140,116 | 2/1979 | Hampicke | 128/165 |

Primary Examiner—John D. Yasko
Attorney, Agent, or Firm—Knobbe, Martens, Olson & Bear

[57] ABSTRACT

An adjustable disposable splint for use in emergency treatment for dislocations and fractures. The device can be used by persons with only minimum training and can readily be modified in the field for treatment of children or small adults. The devices of the invention are readily usable in connection with adult short arm, long arm and leg fractures and dislocations. Additionally, through simple modification the devices can be used as adult bent elbow splints and in the treatment of small children.

4 Claims, 6 Drawing Figures

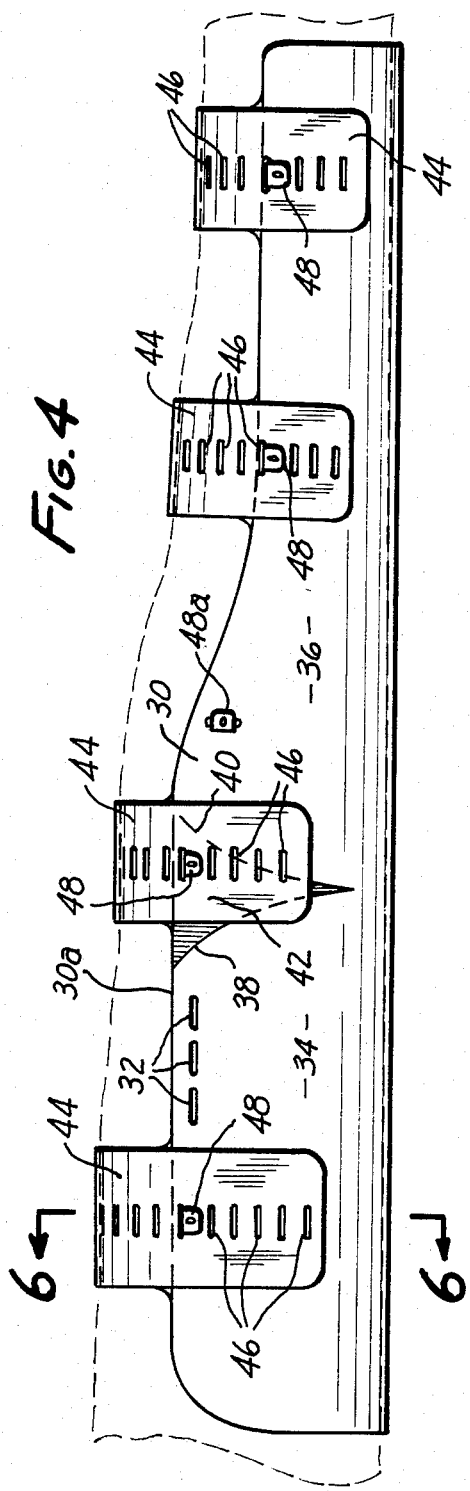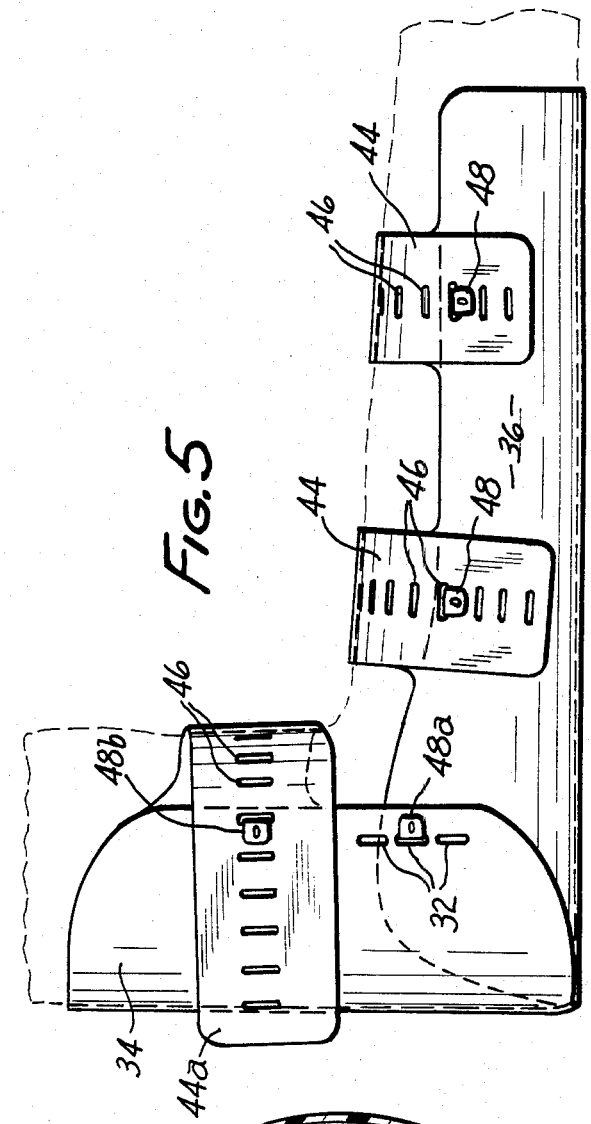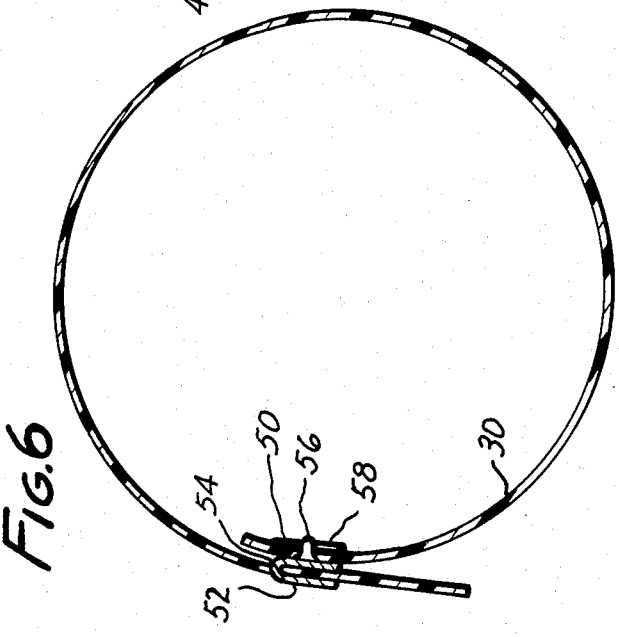

SPLINT AND METHOD OF USING SAME

BACKGROUND OF THE INVENTION

1. Field of the Invention

The present invention relates generally to splints and the method of using same. More particularly the invention concerns adjustable, disposable splints for emergency care of dislocations and fractures. The splints of the invention can readily be modified in the field for use in immobilizing the arms or legs of both children and adults of various sizes.

2. Discussion of the Prior Art

Prompt emergency care of fractures and dislocations is of great importance to prevent or minimize complications associated with such injuries. These complications include pain caused by the unrestricted movement of bone ends and fragments, damage to soft tissues and damage to blood vessels. To avoid these and other complications prompt splinting of the accident victim is vitally necessary.

Splinting may be simply defined as the process used to immobilize fractures and dislocations. Medical experts traditionally follow two age old adages in treating fractures and dislocations. These are, "when in doubt apply splints" and whenever possible "splint 'em where they lie". In recognition of these principles, ambulances, police, fire and other emergency vehicles are generally equipped with splints for emergency use and for immobilizing the fracture during transport of the victim to a hospital or other treatment center.

Numerous types of splints have been suggested in the past. However, many are too complicated, or otherwise contraindicated for emergency aid work, where the apparatus to be used must be simple and easily and quickly applied. A commonly used splint is the so-called Thomas-type splint. This type of splint is slipped over the injured extremity and traction applied so as to provide immobilization of the limb. It is generally recommended, however, that this type of splint be used only by especially trained, professional personnel since the improper application may not only cause severe pain, but may also result in further damage.

Recently there has been developed several new types of emergency splints which use pneumatic principles. These devices typically consist of a double-walled vinyl plastic sack fitted with a closure mechanism, such as a zipper, so that the device can be slipped over the injured extremity, zipped closed and then inflated by lung pressure or an ancillary source of air under pressure such as a small gas bottle. However, use of these devices except by trained professionals can be very dangerous. They should never be inflated to a pressure greater than about 30 millimeters mercury and must be properly located relative to the fracture and carefully supported during the inflation step. If these precautions are not taken, further damage to the victim may result. Additionally, if the interval between application of the inflatable splint and definitive care is prolonged, blood circulation can be dangerously impaired.

Another type of splint commonly used for emergency treatment is an elongated, box-like device typically made of cardboard or other inexpensive material. Such devices are commonly carried in emergency vehicles for use at an accident scene. However, because the devices are easily damaged and are susceptable to deterioration upon prolonged exposure to the elements, they are frequently unusable at the very time they are most needed. Additionally, splints of this type are of crude design, are difficult to use and often fail to adequately support the fracture or dislocation.

The splinting device of the present invention uniquely overcomes the drawbacks of the prior art devices by providing a novel, multipurpose disposable splint which can be used on adults, or by simple adjustment, can be used on children. The device is made of a durable, yieldably deformable sheet plastic material which is virtually impervious to hostile environments. It is expeditiously adjustable and quickly modifiable to fit persons of various sizes and to rigidly immobilize the limbs of the patient in the area of the fracture or dislocation.

SUMMARY OF THE INVENTION

The splinting device of the present invention comprises a generally planar shaped body portion which is yieldably deformable from a first open position to a second closed position wherein the area of the fracture or dislocation is closely surrounded by the body portion; and a fastener mechanism for securing the body portion in the closed position. The fastening mechanism comprises a plurality of longitudinally spaced apart, elongated straps extending transversely of the body portion; and a plurality of spaced apart first locking elements affixed to the body portion along the outer edge thereof. The locking elements are closely receivable within one of several apertures provided in the straps to secure the device in a closed position. The body portion also includes indicia dividing the planar body into first and second areas. A plurality of spaced apart second locking elements are provided along the dividing indicia. Being a thin plastic material the body portion can conveniently be cut along the indicia to form a splint having a smaller body portion which is co-extensive with the second area. The splint thus formed being smaller than the unmodified device is ideal for use with children or with small adults.

An object of the present invention is to provide a splint of the character described which is easily used in the field by persons having a minimum of first aid training.

Another object is to provide a splint which is fully adjustable and can easily be modified for use with both children and adults.

A further object is to provide a splint which is substantially impervious to damage caused by rough handling and storage in hostile environments.

Another object of the invention is to provide a device of the aforementioned character which can be used as a long arm splint or in the alternative can readily be modified for use in immobilizing the elbow joint and the upper arm.

Still another object of the invention is to provide a splinting device which is inexpensive to manufacture so that after emergency use it economically can be discarded.

These and other objects will become apparent from the description which follows.

BRIEF DESCRIPTION OF THE DRAWINGS

FIG. 4 is a side elevational view of another form of the splint of the invention adapted for use as an adult long arm splint, an adult long arm bent elbow splint and a leg splint.

FIG. 5 is a side elevational view of the splint shown in FIG. 4 but cut along the center portion thereof to form the adult bent elbow splint.

FIG. 6 is a cross-sectional view taken along lines 6—6 of FIG. 4 showing the method by which the splint straps are adjustably interconnected with the splint body.

DESCRIPTION OF THE PREFERRED EMBODIMENTS

Figure 1:
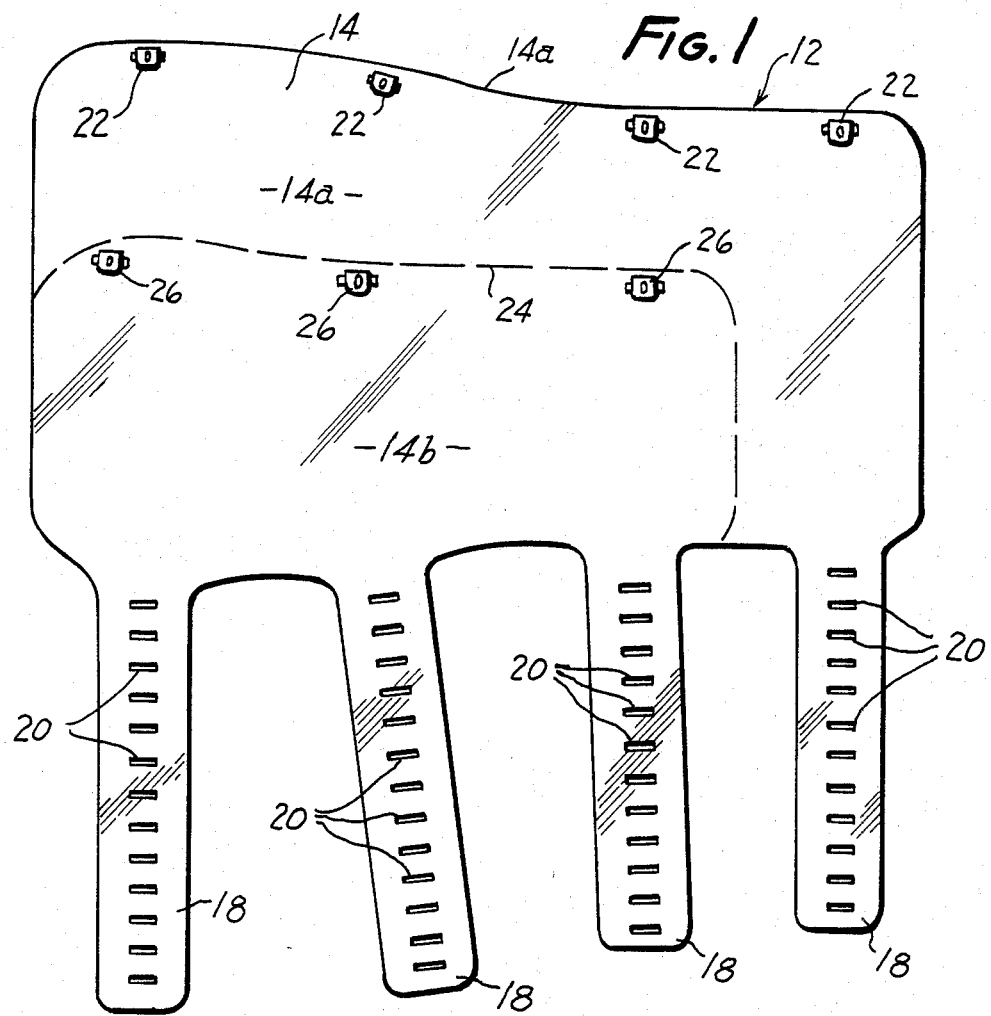
FIG. 1 is a plan view of one embodiment of the invention in the form of a combination adult short arm and pediatric short arm splint.
Figure 2:
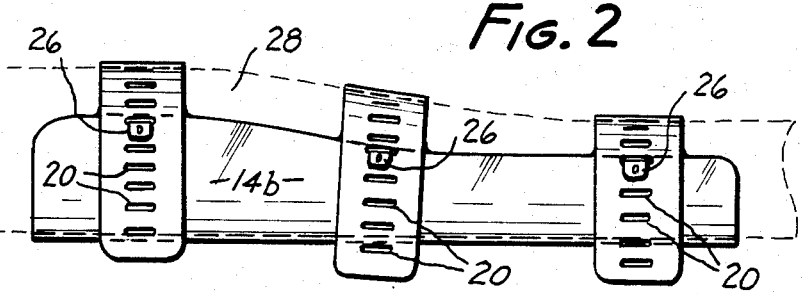
FIG. 2 is a side elevational view of the splint shown in FIG. 1 having been cut down for pediatrics use and shown in an operative position about the arm of the child.
Figure 3:
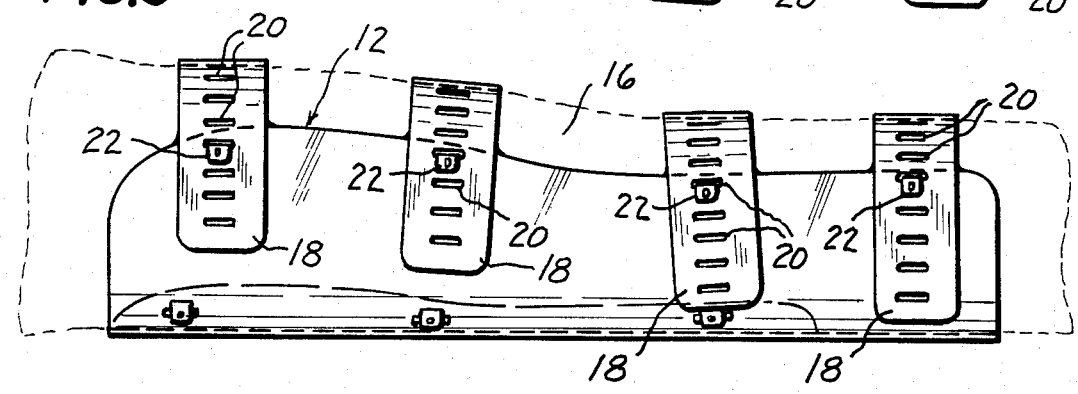
FIG. 3 is a view similar to FIG. 2 but showing the splint of FIG. 1 as it would appear in use for an adult short arm application.

Referring to the drawings and particularly to FIGS. 1 through 3, one form of the splint of the present invention is thereshown and is generally designated by the numeral 12. The device comprises a generally planar shaped body portion 14 which is yieldably deformable from a first open position as shown in FIG. 1, to a second closed position, as shown in FIG. 2, wherein the area of the fracture or dislocation is closely surrounded by body portion 14. As indicated in FIG. 3, the splint of this embodiment of the invention, commonly referred to as a short arm splint, is ideally suited for use in immobilizing the arm 16, of the patient (shown in dotted lines in FIG. 3).

Also forming a part of the embodiment of the invention shown in FIGS. 1 through 3, is fastening means for securing the body portion 14 in the second position shown in FIG. 3. These fastening means comprise a plurality of longitudinally spaced apart elongated straps 18 each having a plurality of spaced apart apertures 20 formed therein and a plurality of spaced apart first locking elements 22. While the body portion 14 and straps 18 can be constructed of various flexible materials, these portions are preferably integrally formed from a thin sheet of plastic material such as polyvinyl, polyethylene or other flexible and durable plastic material.

Locking elements 22 are securely affixed to body portion 14 along a first longitudinally extending line disposed proximate the outer edge 14a of the body portion 14. As best seen by referring to FIGS. 3 and 6, these locking elements 22 are removably receivable within the apertures 20 and function to interconnect the straps to the body along the edge 14a of the body portion. It is to be understood that depending upon the size of One of several of the various apertures 20 provided in the straps 18 may be selected for insertion of the locking elements 22 depending upon the size of the arm 16 of the patient. The wide range of adjustability provided by the fastening means insures that the splint can be securely positioned about the arm 16 so as to totally immobilize the limb in the area of the fracture or dislocation.

A unique aspect of the present invention is the ability to readily modify the device for use in immobilizing various limbs of the body and for use with small patients or children. To accomplish such modifications, body portion 14 includes indicia, shown here in the form of a dotted line 24, which is inscribed on the upper surface of body portion 14. This indicia divides body portion 14 into first and second areas 14a and 14b, the second area 14b being encompassed within the first area 14a. As best seen in FIG. 1, a plurality of second longitudinally spaced apart locking elements 26 are affixed to body portion 14b along a first line located proximate the outer portion of line 24.

With the arrangement thus described and as illustrated in FIG. 1, the body portion 14 is adapted to be cut along line 24 to form a splint having a body portion coextensive with second area 14b. The splint thus formed, being substantially smaller than the device before modification, is readily adaptable for use with children or with small adults. Referring to FIG. 2, the splint, as modified, is illustrated in a closed position about the arm 28 of a small adult or child. In this position, locking elements 26 have been closely received within apertures 20, formed in straps 18. Once again, the plurality of apertures 20 provided in the straps 18 permit the proper positioning of the body portion 14b of the splint securely about the patient's arm 28 so as to completely immobilize it in the area of the fracture or dislocation. The strap 18 being formed of a thin plastic, or other flexible material, can be cut if necessary after the device is locked in its closed position about the arm 28 of the patient.

Turning now to FIGS. 4, 5 and 6, there is shown another form of the splinting device of the present invention. This device is of similar construction to that illustrated in FIGS. 1 through 3, but is uniquely adaptable for use as a leg splint, as an adult long arm splint, or, upon modification, as a long arm bent elbow splint.

Referring to FIG. 4, the device of this form of the invention is shown in use as a long arm splint. However, this device, or a slightly larger version thereof, can also be used as a leg splint. The device is preferably constructed of a thin plastic material and comprises a generally planar shaped body portion 30, which is yieldably deformable from a first open position to a second closed position as shown in FIG. 4, wherein the area of the fracture or dislocation in the patient's arm is closely surrounded by the body portion 30. Body portion 30 is provided with at least one first aperture 32 located proximate one edge 30a of the body portion 30 (three apertures are shown in FIG. 4). Body portion 30 is also provided with indicia inscribed thereon intermediate the ends thereof to define first and second end portions 34 and 36. In the form of the invention shown in FIGS. 4 through 6, the indicia comprises curved lines 38 and 40 extending inwardly from the upper edges (as shown in FIG. 4) of body portion 30. These curved lines 38 and 40 extend inwardly and taper toward the center of body portion 30 so as to define generally "V" shaped segments 42 disposed intermediate end portions 34 and 36. Although not shown in the drawings, a "V" shaped segment 42 formed by indicia 38 and 40 is also inscribed upon the opposite side of body portion 30 from that visible in FIG. 4.

The splinting device of this form of the invention also includes a plurality of longitudinally spaced apart elongated straps 44 provided with a plurality of spaced apart second apertures 46 formed therein. A plurality of spaced apart first locking elements 48 are affixed to body portion 30 proximate edge 30a thereof. Locking elements 48 are closely receivable within seond apertures 46 and function to removably interconnect straps 44 with body portion 30 along one edge thereof. One of the locking elements, specifically identified in FIG. 4 by the numeral 48a, is disposed intermediate the ends of body portion 30 and is vertically rather than horizontally oriented. As illustrated in FIG. 5 this element is closely receivable in one of the apertures 32 formed in body portion 34.

As illustrated in FIG. 5, the body portion 30 of the present form of the invention is adapted to be cut along indicia lines 38 and 40 so that first end portion 34 of the splint can be moved perpendicularly relative to the second portion 36 in the manner shown in FIG. 5 to enable locking element 48a to be closely received within one of the apertures 32 provided in body portion 34. With this arrangement, the splint can be used in the manner shown in FIG. 5 to encase and immobilize the upper arm, the forearm and the elbow of the victim. Such versatility can be extremely valuable in emergency situations arising in the field.

Referring now to FIG. 6, the details of construction of the locking elements is thereshown. It is to be understood that the construction of the locking elements 22, 26 and 48 are identical and that the description which follows will apply to the construction of each of these locking elements. As shown in FIG. 6, the locking element can be seen to comprise a first leg 50, connector means carried by the first leg for interconnecting the element with the body portion, a second leg 52 spaced apart from and extending generally parallel to first leg 50 and a third leg 54 interconnecting said first and second legs. In the form of the invention shown in FIG. 6, the connector means comprises at least one inwardly extending ear portion 56 interconnected with first leg 50. The ear, or ears, 56 are adapted to protrude through the body portion 30 and into an apertured securement plate 58. With the plate 58 in close engagement with the inner wall of body portion 30 and the leg 50 in close engagement with the outer wall of the body portion, ear or ears 56 are bent over to securely affix the locking element in position relative to the body portion of the splint.

Operation

The several forms of the invention shown in the drawings can conveniently be stored in an emergency vehicle in the trunk or behind the seat of the vehicle. Additionally, the devices may be stored in industrial or home first aid areas for substantial lengths of time without fear of degredation of the material. Being constructed of a material which is substantially impervious to hostile environments, heat, moisture, dirt and most chemicals will not degrade the splint devices.

When an emergency situation arises and it is necessary to splint the victim prior to transport to an emergency care facility, the paramedic or other person trained in first aid can quickly select the appropriate splint for use in splinting the fractured or dislocated limb. For example, if the injured person is an adult and the injury is to the arm, the form of the invention shown in FIGS. 1 and 3 may be selected. The arm of the patient is gently extended, placed centrally of the body portion 14 of the splint and the straps 18 are then encircled over the arm. The locking elements 22 are then inserted into the appropriate apertures 22 formed in the straps 18 so as to securely position the splint about the arm of the patient in the manner shown in FIG. 3.

If the victim is a small adult or a child, the paramedic, using scissors or a knife, can quickly cut the form of the splint shown in FIG. 1 along the dotted line 24. The splint thus formed may be used to immobilize the arm 28 within the body portion 14b of the splint in the manner shown in FIG. 2.

If the fracture or dislocation is in the leg or in the upper or lower arm, the form of the invention shown in FIGS. 4 and 5 may be selected. For example, if it is desired to immobilize the leg or the long arm of the victim, the device is used in the manner previously described and as illustrated in FIG. 4, with the body portion 30 of the device surrounding the injured limb and the straps 44 appropriately secured by locking elements 48 to hold the splint in location securely about the damaged limb.

If the injury is to the upper arm or to the elbow, and it is desirable to immobilize the arm in the bent elbow configuration shown in FIG. 5, the paramedic or other person trained in first aid, using scissors or a knife, can quickly cut the splint on both sides of body portion 30 along curved lines 38 and 40. This permits end portion 34 of the splint to be employed to support the upper arm portion of the victim while end portion 36 can be used to support the forearm of the victim. With the splint bent in the perpendicular orientation shown in FIG. 5, locking elements 48 are first inserted into the appropriate apertures 32 formed on either side of end portion 34. As shown in FIG. 5, this will maintain the splint in the bent arm or right angle configuration shown in FIG. 5. The arm of the patient is then gently bent and inserted into the splint. Using the strap designated in FIG. 5 as 44a and using the locking element designated in FIG. 5 by the numeral 48b, the strap is securely positioned about the upper arm of the patient. The forearm of the patient is then securely encapsulated within end portion 36 of the splint by use of the remaining straps 44 which are secured in position by locking elements 48.

It is to be understood that the configuration of the devices shown in the drawings is exemplary only and that various configurations may be used for particular splinting operations without departing from the intent of the invention. Through suitable variations within the scope of the invention, the splinting devices can also be used on animals as well as humans. These devices may be of slightly different configuration and may have a greater or lesser number of securing straps, but will function in the manner described herein.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A device for use in splinting fractures and dislocations, comprising:
   (a) a generally planar shaped body portion yieldably deformable from a first open position to a second closed position wherein the area of the fracture or dislocation is closely surrounded by said body portion;
   (b) fastening means for securing said body portion in said second position, said means comprising:
      (1) a plurality of longitudinally spaced apart, elongated straps extending transversely of said body portion, each said strap having a plurality of spaced apart apertures formed therein; and
      (2) a plurality of spaced apart first locking elements affixed to said body portion along a first longitudinally extending line, said elements being receivable within said apertures for interconnecting said straps to said body along said first line; and (c) indicia dividing said body portion into first and second areas, said second area being encompassed within said first area, said device also being provided with a plurality of second, longitudinally spaced apart locking elements, said first locking element being disposed along a first line located proximate an edge portion of said first area and said second locking element being disposed along a second line disposed proximate an edge portion of said second area.

2. A device as defined in claim 1 in which said body portion is adapted to be cut along said indicia to form a splint having a body portion coextensive with said second area, said splint thus formed being substantially smaller than said device before modification and, therefore, adaptable for use with children or with small adults.

3. A device for use in splinting fractures and dislocations of the upper and lower arm, comprising:

(a) a generally planar shaped body portion yieldably deformable from a first open position to a second closed position wherein the area of the fracture or dislocation is closely surrounded by said body portion, said body portion having at least one first aperture provided proximate one edge thereof and including indicia inscribed thereon intermediate the ends thereof to define first and second end portions;

(b) fastening means for securing said body portion in said second position, said means comprising:
  (1) a plurality of longitudinally spaced apart, elongated straps extending transversely of said body portion, each said strap having a plurality of spaced apart second apertures formed therein; and
  (2) a plurality of spaced apart first locking elements affixed to said body portion proximate said one edge thereof, said elements being receivable within said second apertures for interconnecting said straps to said body along said first line, one of said locking elements disposed proximate said indicia being receivable in said second aperture provided in said body portion, said body portion being adapted to be cut along said indicia whereby said first end portion can be moved perpendicularly with respect to said second end portion to enable said one of said locking elements to be received within said first aperture.

4. A device as defined in claim 3 in which said indicia comprises curved lines extending inwardly from each edge of said body portion to define a pair of generally "V" shaped segments located intermediate the ends of said body portion.

* * * * *